United States Patent
Laghi

(10) Patent No.: US 8,257,531 B2
(45) Date of Patent: *Sep. 4, 2012

(54) METHOD OF MAKING AN EXTERNAL BREAST PROSTHESIS

(75) Inventor: Aldo A. Laghi, Clearwater, FL (US)

(73) Assignee: Alps South, LLC, Clearwater, FL (US)

( * ) Notice: Subject to any disclaimer, the term of this patent is extended or adjusted under 35 U.S.C. 154(b) by 583 days.

This patent is subject to a terminal disclaimer.

(21) Appl. No.: 12/383,490

(22) Filed: Mar. 25, 2009

(65) Prior Publication Data

US 2009/0183822 A1 Jul. 23, 2009

Related U.S. Application Data

(62) Division of application No. 11/222,288, filed on Sep. 8, 2005, now Pat. No. 7,766,963.

(51) Int. Cl.
*B65B 51/02* (2006.01)
(52) U.S. Cl. ..................................... 156/145; 428/304.4
(58) Field of Classification Search .................. 156/145; 428/304.4
See application file for complete search history.

(56) References Cited

U.S. PATENT DOCUMENTS

| | | | | |
|---|---|---|---|---|
| 5,370,688 A * | 12/1994 | Schulz et al. | ...................... | 623/7 |
| 5,545,220 A * | 8/1996 | Andrews et al. | ................... | 623/8 |
| 2002/0058135 A1* | 5/2002 | Yates | ......................... | 428/304.4 |
| 2002/0107431 A1 | 8/2002 | More | | |
| 2002/0193878 A1* | 12/2002 | Bowman et al. | ................... | 623/7 |
| 2005/0220896 A1* | 10/2005 | Laghi | ............................ | 424/618 |

* cited by examiner

*Primary Examiner* — Katarzyna Wyrozebski Lee
*Assistant Examiner* — Vishal I Patel
(74) *Attorney, Agent, or Firm* — Shumaker, Loop & Kendrick, LLP; Henry J. Recla

(57) ABSTRACT

A method of making an external breast prosthesis by forming an elastomeric skin in the form of a human breast surrounding an inner material such as a silicone gel or hydrogel. The elastomeric skin can be formed from a front skin and a rear skin, and the skins can be made of a soft styrenic elastomer having attributes similar to a gel. At least the front skin is formed by mixing together a polymer, a plasticizing oil and at least one non-volatile additive to form a mixture, heating the mixture, forming the mixture into a front elastomeric skin, and cooling the mixture thereby allowing the non-volatile additive to precipitate to the outer surface of the outer skin to form a cratered outer surface that is substantially soft to the touch and that tends to maintain the skin in a pliable yet pre-defined shape.

12 Claims, 7 Drawing Sheets

METHOD OF MAKING AN EXTERNAL BREAST PROSTHESIS

This application is a divisional of U.S. nonprovisional application Ser. No. 11/222,288 filed on Sep. 8, 2005 and now U.S. Pat. No. 7,766,963, which is herein incorporated by reference.

FIELD OF THE INVENTION

The invention relates to prosthetic devices, and in particular to breast prostheses and methods of making such prostheses.

BACKGROUND OF THE INVENTION

External breast prostheses are artificial breast forms that can be worn after a surgery or other treatment in which the breast has been altered or removed. For example, external breast prostheses are available for women who have had a mastectomy or lumpectomy to remove a breast cancer, and to those who have uneven or unequal sized breasts resulting from radiation or reconstruction procedures.

A mastectomy is a common treatment for breast cancer that involves surgically removing the breast or a portion of the breast. A modified radical mastectomy is the most common type of mastectomy performed today. This procedure involves removing the breast, nipple/areolar region, and often the axillary (underarm) lymph nodes. Other types of mastectomies include simple mastectomy which generally involves removing the breast but no lymph nodes, and partial mastectomy which generally involves removing a cancerous or otherwise abnormal portion of the breast tissue along with a margin of normal breast tissue.

An external breast prosthesis can be worn to help replace the appearance and feel of a breast removed or altered by surgery. Such replacement is often not only for cosmetic, psychological and emotional reasons, but also can provide physiological benefits as well. For example, some breast prostheses are weighted as a therapeutic measure to replace the weight of the lost breast. When fitted with a breast prosthesis that approximates the size and weight of the remaining breast, the weight equilibrium of the body may be kept in balance following surgery to help avoid musculoskeletal problems such as lower back and neck pain which are common following a mastectomy.

Currently available external breast prostheses include entire breast forms and partial forms. Partial breast prostheses are commonly known as equalizers. Breast prostheses can be symmetrical (i.e., they can be turned to fit either side of the body) or asymmetrical (i.e., they fit only the right or the left side). Prostheses can be attached to the skin using an adhesive or other attachment mechanism. Alternatively, a breast prosthesis may be worn inside of a garment such as a mastectomy bra which includes a pocket or other feature to hold the prosthesis in place. Prefabricated prostheses can come in various shapes, sizes and skin tones and may be custom fabricated using a mold that is taken of the breast and/or chest wall prior to or after surgery.

Most external breast prostheses available today are made of a gel, either silicone or water based, contained in a plastic film that acts as a skin to contain the gel. The film is generally made of polyurethane and is substantially inelastic. Existing external breast prostheses incorporating such plastic film have a number of drawbacks and deficiencies. For example, the film has an unnatural, relatively inflexible feel that is substantially different to the touch from the feel of human skin. Also, the film forms hundreds of wrinkles as the prosthesis is deformed from its original molded shape. In fact wrinkles generally are always present on the prosthesis skin even when such prosthesis is donned. Also, the inner gel used in such a prosthesis must have its own shape, as the film does not have the inherent ability to force the gel into a predetermined shape.

Other available external breast prostheses consist of a piece of foam in the shape of a human breast. Such foam prostheses generally lack the consistency, feel, appearance and weight of gel-filled prostheses and are therefore of limited functionality and performance. In some cases, such prostheses are used temporarily following surgery, for example to provide a basic breast form that is light-weight to minimize discomfort during healing of the surgical scars.

Some existing breast prostheses have two or more chambers defined by polyurethane films, where each chamber is filled with a gel of different consistency or firmness. Like existing single-chambered prostheses, such multi-chambered prostheses employ a thin polyurethane outer barrier that is substantially inelastic and lacking characteristics that provide the look and feel of human skin.

Accordingly, there is a need in the art to provide improved external breast prostheses having the texture, appearance, and elasticity of a normal human breast.

SUMMARY OF THE INVENTION

The present invention overcomes the disadvantages of the current art and provides external breast prostheses and methods of making such prostheses with improved skin and other features for providing the texture, appearance, firmness and elasticity approximating that of a normal human breast.

In one embodiment, an external breast prosthesis has one or more elastomeric skins, which form the outer surface of the prosthesis, and that define one or more inner chambers filled with an inner material, for example a liquid or a gel. For example, such an external breast prosthesis can have a front skin comprising an elastomeric polymer configured and dimensioned to approximate the shape of a human breast, wherein the skin surrounds a cavity filled with a gel such as a hydrogel or a silicone gel. In certain embodiments, the skin comprises a front portion, or front skin, and a rear portion, or rear skin, wherein the front and rear skins are joined about a perimeter of the prosthesis.

In some embodiments, one or more skins of an external breast prosthesis comprise a triblock copolymer, for example a copolymer comprising styrene and at least one of ethylene, butadiene, butylene, propylene, or isoprene. For example, an external breast prosthesis comprises a front and/or rear skin comprising a hydrogenated poly(styrene-b-isoprene), a hydrogenated poly(styrene-b-isoprene-b-styrene), a hydrogenated poly(styrene-b-butadiene-b-styrene), a hydrogenated poly(styrene-b-isoprenelbutadiene-b-styrene), or combinations thereof. In certain embodiments, the front and/or rear skin comprises any of polystyrene-b-poly(ethylene/propylene) (SEP), polystyrene-b-poly(ethylene/propylene)-b-polystyrene (SEPS), polystyrene-b-poly(ethylene/butylene)-b-polystyrene (SEBS), or polystyrene-b-poly(ethylene-ethylene/propylene)-b-polystyrene (SEEPS), or any combination thereof.

The front and/or rear skins may also comprise selected amounts of one or more plasticizing oils, for example, a paraffinic oil, naphtenic oil, a mineral oil, or a synthetic oligomer of a polybutene, a polypropene, or a polyterpene oil.

In other embodiments, a breast prosthesis with an outer skin of a triblock copolymer, for example comprising a triblock copolymer and a plasticizing oil, may further comprise one or more additives to optimize the feel of the skin. Suitable additives are described herein and, for example, in the applicant's co-pending U.S. patent application Ser. No. 10/817,612 filed Apr. 2, 2004, entitled Precipitation of Additives in Over-Saturated Triblock Copolymer Elastomers, which is incorporated by reference herein in its entirety.

External breast prostheses according to the present invention can comprise a shaped gel or an amorphous gel, and such gel may be, for example, silicone-based, water-based, and/or based on other materials that do not act as a solvent of the elastomeric skins. In some embodiments, the inner material has its own shape, for example in the shape of a human breast, and can have shape-memory properties. In other embodiments, the inner material is substantially shapeless and conforms to a shape defined by the skins or other barriers of the external breast prosthesis.

In other embodiments, an external breast prosthesis comprises a front skin and a base, or rear, skin, wherein the front and rear skins are of different thicknesses. For example, the base skin may be thicker than the front skin to provide a desired amount of firmness or structural support.

In other embodiments, an external breast prosthesis comprises two or more internal cavities or chambers. Each chamber may be defined, for example, at least in part by elastomeric skins and may be filled with a liquid, a solid, or a gel having desired characteristics. For example, such a prosthesis may include a front chamber with a first filling material of a particular consistency or firmness, and a rear chamber having a filling material of a different consistency or firmness.

A method of making an external breast prosthesis according to an embodiment comprises combining a polymer such as a styrene triblock copolymer with a plasticizing agent, for example a mineral oil, and processing the mixture into desired shapes to make front and rear elastomeric skins of a prosthesis. Such processing can involve, for example, heating and forming the material, e.g., by molding or thermoforming or a combination thereof, into a desired shape. In some embodiments, additives are used to provide desired mechanical properties for the elastomeric skins. The skins can be joined or sealed together, for example by an adhesive or a heat seal. One or more cavities defined by the skins can then be filled through an access site with an inner material such as a liquid or a gel, for example a silicone gel or a hydrogel. The access site can then be sealed and the excess material can be trimmed.

In other embodiments, an inner material such as a gel can include microspheres or other particles or devices to optimize the density and/or weight of the prosthesis.

BRIEF DESCRIPTION OF THE DRAWINGS

The invention and further developments of the invention are explained in even greater detail in the following exemplary drawings. The present invention can be better understood by reference to the following drawings, wherein like references numerals represent like elements. The drawings are merely exemplary to illustrate certain features that may be used singularly or in combination with other features and the present invention should not be limited to the embodiments shown.

DETAILED DESCRIPTION

Figure 1B:
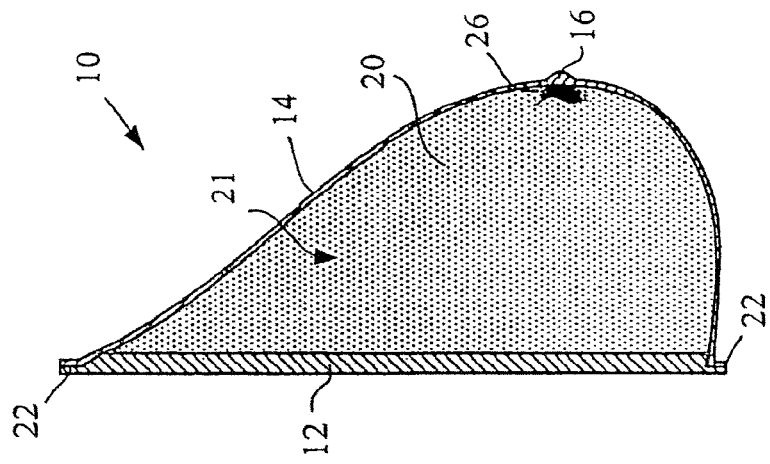
FIG. 1B is a cross-sectional view illustration of an embodiment of the external breast prosthesis of FIG. 1 taken along line A-A.
Figure 1A:
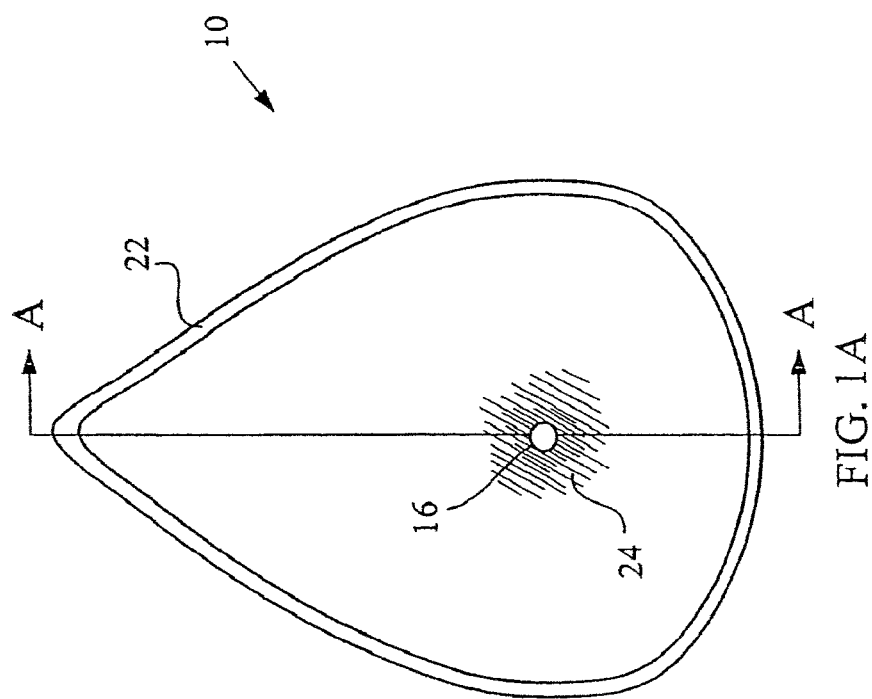
FIG. 1A is a front view illustration of an embodiment of an external breast prosthesis according to the present invention.

FIGS. 1A and 1B depict front and cross-sectional views, respectively, of an external breast prosthesis 10 according to an embodiment of the present invention. Prosthesis 10 includes a base, or rear skin 12, a front skin 14, and an inner material 20 disposed within an inner cavity or chamber 21 between and confined by skins 12 and 14. Front skin 14 and/or rear skin 12 can be made of an elastomer such as a soft elastomer. For example, elastomeric skins 12 and 14 can be substantially soft to the touch and have an elastic memory that tends to maintain the skin in a pliable yet pre-defined shape.

In some embodiments, rear skin 12 and/or front skin 14 comprise a triblock copolymer or combinations thereof. For example, suitable elastomeric materials include styrenic triblock copolymers, such as a hydrogenated poly(styrene-b-isoprene), a hydrogenated poly(styrene-b-isoprene-b-styrene), a hydrogenated poly(styrene-b-butadiene-b-styrene), a hydrogenated poly(styrene-b-isoprenelbutadiene-b-styrene), or combinations thereof. In certain embodiments, the front and/or rear skin comprises any of polystyrene-b-poly(ethylene/propylene) (SEP), polystyrene-b-poly(ethylene/propylene)-b-polystyrene (SEPS), polystyrene-b-poly(ethylene/butylene)-b-polystyrene (SEBS), or polystyrene-b-poly(ethylene-ethylene/propylene)-b-polystyrene (SEEPS), or any combination thereof.

An oil or other plasticizing agent (also referred to herein as a plasticizer) can be added to the triblock copolymer in order to provide desired mechanical properties, such as elasticity, softness (or hardness), and elongation, tear and tensile strength characteristics of the resulting elastomer. For example, in some embodiments, suitable mechanical properties include: (a) hardness between approximately 10 to 70 durometer on the Shore 00 scale, more preferably about 25 durometer on the Shore 00 scale; (b) ultimate elongation of approximately 300 to 2000 percent, more preferably about 1500 percent; and/or (c) tensile modulus at 300 percent elongation of between about 5 to 300 psi, more preferably about 30 psi. One or more other additives can also be included in or added to such formulations in order to provide a desired tactile feel, and/or to optimize mechanical properties or other characteristics of the front 12 or rear 14 skin, or portions of such skins.

Skins 12, 14 can be fused or joined in a seal 22, for example by an adhesive or a heat seal, that confines inner material 20 within inner cavity or chamber 21 between skins 12 and 14. Seal 22 can be any desired width and/or thickness, e.g., between about 2 to 10 millimeters wide and about 0.5 to 5 millimeters thick, more preferably between about 2 to 6 millimeters wide and about 1 to 2 millimeters thick. Seal 22 can be a single seal joining front skin 14 and rear skin 12 about a perimeter of prosthesis 10 as shown, or can comprise multiple seals or joints in any desired configuration. One skilled in the art will appreciate that, while some embodiments described herein can include distinct front and rear skins 14 and 12 that are adhered, fused, or otherwise joined at a seal 22, other embodiments of prosthesis 10 include a single contiguous skin surrounding cavity or chamber 21, e.g., with no seam or seal 22, and are intended within the scope of the present invention.

Elastomeric skins 12, 14 can be substantially thicker and more elastic and resilient than polyurethane films used in existing breast prostheses, thereby providing a more natural appearance. In some embodiments, for example, front skin 14 has an average thickness between about 0.1 to 3 mm, preferably about 1.5 mm; and rear skin 12 has an average thickness between about 0.3 to 5 mm, preferably about 3 mm. Skin 12 and/or skin 14 need not have a uniform thickness. In some embodiments, front skin 14 near perimeter seal 22 is relatively thick, e.g., between about 3 to 10 mm thick, preferably approximately 5 mm thick. Such increased thickness may help to provide support for a more natural draping of the prosthetic breast 10 when the bust of the patient is in the erect position.

Elastomeric skins 12, 14 can be made substantially without wrinkles, particularly compared with the wrinkles that are prevalent in existing prostheses. Skins 12, 14 can have an appearance, firmness, elasticity, texture and other characteristics that approximate human skin. For example, a "natural" firmness and feel can be represented by measurement of Shore 00 durometer, with a desirable value of about 20 to 30 Shore 00 durometer, more preferably about 25 Shore 00 durometer. In some embodiments, a "natural" texture and smoothness can be obtained by precipitation of additives, which provides a texture of having microscopic craters similar to human skin.

Skins 12, 14 can be the same or different thickness as each other and/or each can have a variable thickness, for example depending upon the desired shape, firmness, weight, resiliency, or other characteristics of prosthesis 10. Relative thicknesses of skins 12, 14 can also be related to materials used in skins 12, 14 and in filling 20. For example, in some embodiments, rear skin 12 is thicker than front skin 14 as shown in FIG. 1B. In other embodiments, front skin 14 may be thicker than rear skin 12. In specific embodiments, front and rear skins 14 and 12 can comprise different compositions of polymers, oils, additives and the like to provide desired characteristics.

Determination of a desired amount and/or pattern of skin thickness variations can depend upon the size of prosthesis 10 and the weight of filling 20. For example, if filling 20 is of the amorphous or shapeless type that conforms to the shape of skins 12, 14, one should consider that the larger the breast the greater the weight. (e.g., according to a factor "L" to the third power, where "L" is an average linear dimension of the breast). Assuming the modulus of elasticity of an elastomeric skin is kept constant, the ability of such skin to hold its shape is a function of its thickness and the "L" linear dimension of the skin to the single power. Therefore, in general, larger breast prostheses may require thicker skins for the same "draping". Also in the area near seal 22 where the front and the rear skin are joined, for example, front skin 14 may be substantially thicker in order to help maintain a desired shape, both when the patient is standing or sitting in an upright position as well as when the patient is laying down in a supine position.

Inner material 20 can be any type of suitable filling to provide desired properties such as weight, consistency, resiliency, firmness and feel, and to approximate such properties of a normal human breast. Gels adequate for this purpose can include silicone gels as well as water based gels, or hydrogels s, for example gels used in wound care or food applications. Other filling 20 material may be used instead of or in addition to silicone gels or s, including for example liquids or gels that are chemically and physically compatible with the elastomer of the skins 12, 14 of the prosthesis. In some embodiments, inner material 20 is substantially shapeless or amorphous, and the shape of prosthesis 10 is defined by skins 12, 14. In other embodiments, inner material 20 can have its own shape that helps define the shape of prosthesis 10. Inner material 20 and/or skin 14 and/or skin 12, can comprise one or more coloring agents to provide any desired color or pattern of colors, e.g., a color approximating a natural skin tone of a Caucasian user, an African-American user, an Asian user, or any other potential or particular user. Suitable coloring agents include, for example, dyes and pigments that are commonly known and used in the industry for providing skin tone coloring to silicone gels in cosmetic covers of hand and leg prostheses. For s, pigments and dyes of the type used in food coloring can be used.

The definition of "gel" can vary from one industry to the next. As used herein, the term "gel" is intended to cover a variety of materials that have a jelly-like consistency, and includes both shaped and shapeless gels. As used herein, shaped gels can maintain their own shape, for example a shape defined during a curing process (e.g., in forming a silicone gel) or with the addition of a thickening agent (e.g., in forming a ). Such gels generally are self-healing when cut and, if deformed, will return to its original shape (i.e., shape memory). As used herein, shapeless, or amorphous, gels generally do not maintain their own shape when deformed. Compared to shaped gels, shapeless gels do not exert appreciable resisting force during or after deformation. Such gels may in fact be liquids with a consistency approximating that of a true gel. In some cases, when such gel-like liquids are rendered lighter by the addition of hollow spheres or by the addition of air, they can maintain their own shape under the effect of the force or gravity, but can be easily deformed and maintain their new shape after the deforming force is withdrawn.

Suitable gels include, for example, but are not limited to:
(a) a polymer gel;
(b) a gel formed by a liquid plus a thickening agent; and
(c) a gel formed by a liquid plus a high surface tension agent.

Any of the above can be used alone or in combination, and can be shaped or shapeless. An example of a suitable polymer for filling 20 is a silicone gel. Examples of a gel that is a liquid plus a thickening agent can include water plus carboxymethyl cellulose (CMC) or polyvinylpyrrolidone (PVP) polyacrylates or polyacrylamides. In this type of gel the thickening agents can swell and trap the water. Examples of gels comprising a liquid plus a high surface tension agent include fumed silica, where the gel generally does not flow under the acceleration of gravity but it can be shaped and reshaped without limitation. This effect can be enhanced even more when the gel is lightened in weight by the addition of fillers as discussed below with respect to other embodiments.

Prosthesis 10 may also include a nipple 16. In some embodiments, nipple 16 is a solid nipple formed or molded as an area of increased thickness in elastomeric skin 14 as shown in FIG. 1B. In other embodiments, skin 14 can be of relatively uniform thickness, with nipple 16 formed as an extended portion or shape of skin 14 filled with gel 20. In some embodiments, a region 26 (also referred to as areola 26) surrounding nipple 16 can be colored to approximate the coloring and likeness of a human areola. This can be achieved, for example, by coloring the areola 26 region of elastomeric skin 14, coloring gel 20 in region underlying nipple 16, or both. In some embodiments, a desired coloring of areola 26 can be achieved by providing a darker color of gel 20 underneath the nipple 16 and allowing it to diffuse into the lighter gel of the surrounding areas. Such practice can result in an effect of uneven fading around the center of areola 26 that closely resembles the natural coloring pattern of the areola of a human breast. Such coloring, in addition to color and additives that may be added to gel 20 and/or skin 14 throughout prosthesis 10, can be used to achieve a desirable depth of coloring overall to approximate the appearance of normal human breast tissue.

Figure 2:
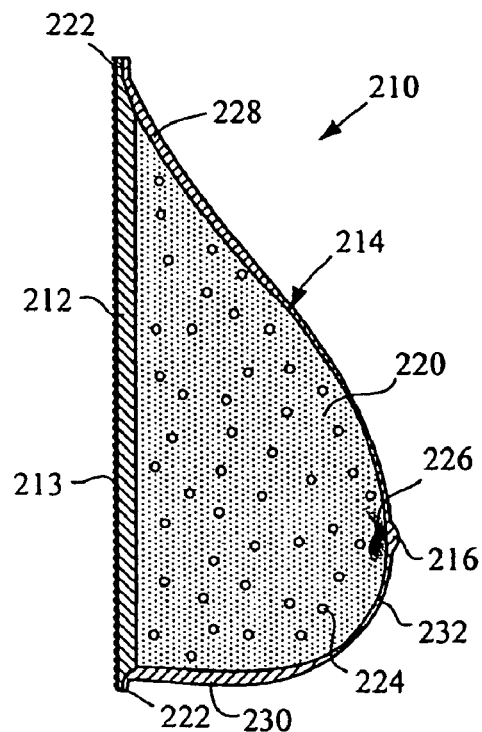
FIG. 2 is a cross-sectional view illustration of another embodiment of an external breast prosthesis having a front skin of varying thickness and a low density inner material.

Referring to FIG. 2, another embodiment of an external breast prosthesis 210 can include a rear skin 212 and a front skin 214 joined by a seal 222. Front skin 214 can include regions of different thickness, for example an upper region 228 and a base region 230 that are substantially thicker or thinner, than a central region 232 surrounding nipple 216 and areola 226. Such variations in thickness of front skin 14 or rear skin 12 may be used to optimize the elasticity of skin and the shape and feel of prosthesis 210.

Like inner material 20 of prosthesis 10, inner material 220 may be a silicone gel, a hydrogel, or any other type of filling suitable for providing desired properties such as weight, resiliency, firmness, feel and appearance. Inner material 220 can comprise or contain particles 224 such as microspheres or other particles that affect the weight or density of prosthesis 210. Particles 224 can be, for example, hollow microspheres such as polymeric or glass beads or microspheres. Examples of suitable microspheres can include acrylonitrile microspheres and glass or ceramic microspheres. Other examples of microspheres may be found, for example in U.S. Pat. No. 5,902,335 to Snyder, Jr., which is incorporated by reference herein in its entirety.

In some embodiments, a fabric is adhered to, embedded within, or otherwise bonded with rear skin 212 and/or front skin 214. For example, as shown in FIG. 2, a fabric 213 can be bonded to rear skin 212. Such fabric 213 can be used, for example, to help maintain a desired shape of the breast prosthesis 210 and limit elongation due to the weight of filling 220. Fabric 213 may be woven or knitted and can comprise polyester, nylon, acrylic, cotton, rayon, or any other desired fabric.

Fabric 213 can be bonded with skin 212 in a variety of ways. For example, in one embodiment, a sheet of fabric 213 is placed on the skin 212 and heat is applied, e.g., using an iron or heated plate, to soften or melt the underlying skin 212 and bind it with the fabric. In another embodiment, an adhesive is used, with or without heat, to apply the fabric. In another embodiment, a mixture of a solvent and gel is used, with or without application of heat, to adhere the fabric 213 to skin 212. In yet another embodiment, fabric 212, is placed in an injection mold during the process of forming skin 212, e.g., fabric 212 is placed in the mold prior to injection of molten elastomer.

Figure 3A:
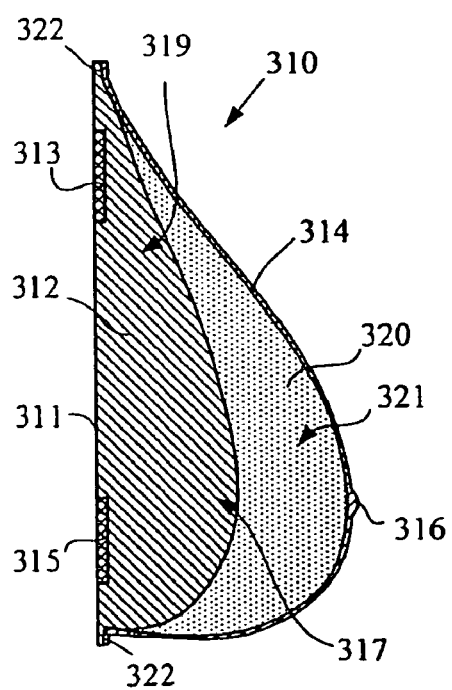
FIG. 3A is a cross-sectional view illustration of another embodiment of an external breast prosthesis.

Referring to FIG. 3A, another embodiment of an external breast prosthesis 310 includes a rear skin 312 that is dimensioned to have a shape that is substantially thicker than front skin 314. Skins 312 and 314 may be formed of a triblock copolymer as described above. Rear skin 312 can have any desired thickness, for example from 10-80 percent of the thickness of prosthesis from outer surface 311 of rear skin 312 to nipple 316. In some embodiments, rear skin 312 is configured and dimensioned to have a varying thickness as shown in FIG. 3A.

Rear skin 312 can include, for example, a central portion 317 that bulges toward nipple 316 and is thicker than an upper, or superior, portion 319 of skin 312. In such embodiments, skin 312 can be dimensioned to approximate the shape of outer skin 314 as shown. In some embodiments, fasteners 313, 315 are integrated within or adhered, fastened or otherwise attached to or with rear skin 312. Such fasteners 313, 315 can be an adhesive material, a hook and loop fastener (e.g., Velcro), or any other material or device that facilitates attachment of prosthesis 310 against the chest of a user (e.g., by direct attachment or adhering to the user's skin, or by attachment to a shirt, bra or other garment or device worn by the user).

Inner material 320 within chamber 321 defined by skins 312 and 314 can be, for example a silicone gel or hydrogel as described above. Rear skin 312 can differ from front skin 314 in terms of firmness and/or other characteristics in order to provide desired firmness, feel, appearance or other properties of prosthesis 310

Figure 3B:
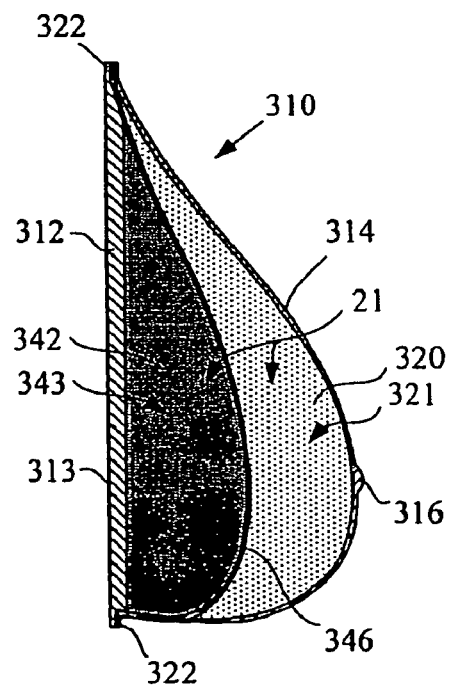
FIG. 3B is a cross-sectional view illustration of another embodiment of the external breast prosthesis of FIG. 3A having multiple chambers.

In another embodiment shown in FIG. 3B, prosthesis 310 can include multiple chambers, such as a first chamber, or front chamber 321 and a second chamber, or rear chamber 343, separated by an inner barrier 346. Inner barrier 346 may be an elastomeric skin such as skin 312 or 314, an elastic or inelastic film, e.g., a polyurethane film, or any other compatible material. Inner material 320 in front chamber 321 can be a silicone gel, a hydrogel, a foam, a liquid or other material of desired consistency. Inner material 342 in rear chamber 343 can also be a silicone gel, a hydrogel, a foam, a liquid, a polymer or other material, and can be the same or different than inner material 320. Inner material 320 can have a consistency, firmness, or other characteristic that is the same or different from that of material 342. Such differences between inner materials 320 and 342, particularly when combined with above-described characteristics of skins 312, 314, can be optimized to provide any desired firmness, feel, weight, appearance or other properties of prosthesis 310.

In specific embodiments according to the present invention, external breast prosthesis 310 comprises inner barrier 346, which is disposed between front skin 314 and rear skin 312 and separates main cavity or chamber 21 into first chamber 321 and second chamber 343. Inner material 320 can be a first gel disposed in first chamber 321, and inner material 342 can be a second gel disposed in second chamber 343, wherein the second gel is the same as or different than the first gel. Inner materials 320 and/or 342 can be, for example, a silicone gel, a hydrogel, another gel, or any combination of gels. For example, in some specific embodiments, materials 320 and 342 are both silicone gels, but of differing stiffness or consistency. In other embodiments, materials 320 and 342 are both s that may be the same or different. In other embodiments, materials 320 and 342 are different types of gels, e.g., one is a silicone gels and the other a hydrogel. In other specific embodiments, material 320 is a foam and material 342 is a gel.

Figure 4:
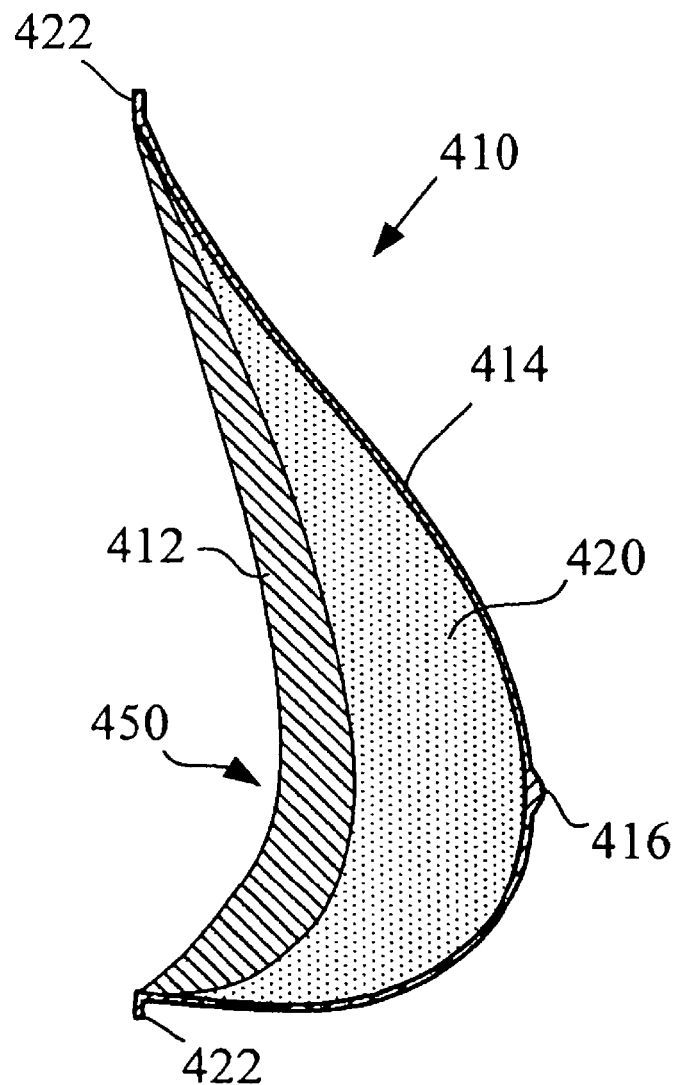
FIG. 4 is a cross-sectional view illustration of an external breast prosthesis having a concave rear skin.

Referring to FIG. 4, other embodiments that may have similar components and characteristics to prostheses 10, 210 and 310 is an external breast prosthesis 410 or partial prosthesis having a rear skin 412 that is shaped and dimensioned to conform to the chest of a patient. For example, rear skin 412 can include a concave rear surface 450 dimensioned to accommodate and fit against the remaining breast tissue or chest wall of a patient, e.g., a mastectomy patient. In other embodiments, concave rear surface 450 can be dimensioned to accommodate, conform with and/or fit against a user's normal breast, as a breast enhancer to augment the size and/or shape of the user's bust. In specific embodiments, prosthesis 410 can be attached to or against the user's breast, or it may be worn within or attached to a brassiere or other garment.

Skins 412 and 414 can be elastomeric skins such as those described herein and each can have any desired shape and thickness to provide desired properties of prosthesis 410. Front skin 414 may comprise a solid nipple 416 with or without surrounding areola coloring as 226 in FIG. 2. Inner material 420 can be a silicone gel, hydrogel, foam or other material, and can contain microspheres or other particles such as particles 224 of FIG. 2. In fact, one skilled in the art will appreciate that breast prostheses according to the present invention can include any combination of features described with respect to the various embodiments herein.

In use, an external breast prosthesis such as 10, 210, 310 and 410 may be adhered or otherwise attached to the skin or undergarment of a patient or other user, or may be integrated with or worn within a bra or other garment or device. Prostheses 10, 210, 310 or 410, or any combination or variations thereof, can be dimensioned and used as a partial breast prosthesis, a full breast prosthesis, and/or a breast enhancer. Rear skin 12, 212, 312, 412 can include, for example, features such as embedded or otherwise bonded fabric, adhesive portions, snap features, adhering features or the like, or other fasteners to facilitate attachment to the patient, garment or device. In some embodiments, the external surface of rear skin 12, 212, 312, 412 and/or front skin 14, 214, 314, 414 is adhesive or partially adhesive, e.g., tacky, sticky or gummy, to facilitate attachment of prostheses 10, 210, 310, 410, respectively.

Kits comprising in a container a breast prosthesis of the invention are also provided. In some embodiments, a kit according to the present invention comprises in one or more containers an external breast prosthesis 10, 210, 310 or 410 and a fastener for adhering or otherwise attaching such prosthesis against a user (e.g., by attachment directly or indirectly to the chest of the user, or to a bra or other garment or device that may be worn by the user and/or may be disposed between the prosthesis and the user). In other embodiments, a kit according to the present invention comprises in one or more containers an external breast prosthesis 10, 210, 310 or 410 and a bra or other garment having pockets or other features for holding such prosthesis in a desired position against a user.

In some embodiments, a prosthesis 10, 210, 310 or 410 is attached to or integrated within a bra or other garment. Such as garment may comprise, for example, a brassiere or a tank top-like undergarment having shoulder straps or other supports attached to a prosthesis and/or to one or more cups or other features configured to hold a prosthesis according to the present invention. Such garments and related prosthesis may be used to replace or enhance the appearance and feel of one or both breasts of a user, and may include a liner, pocket or other feature for holding the prosthesis.

Figure 5:
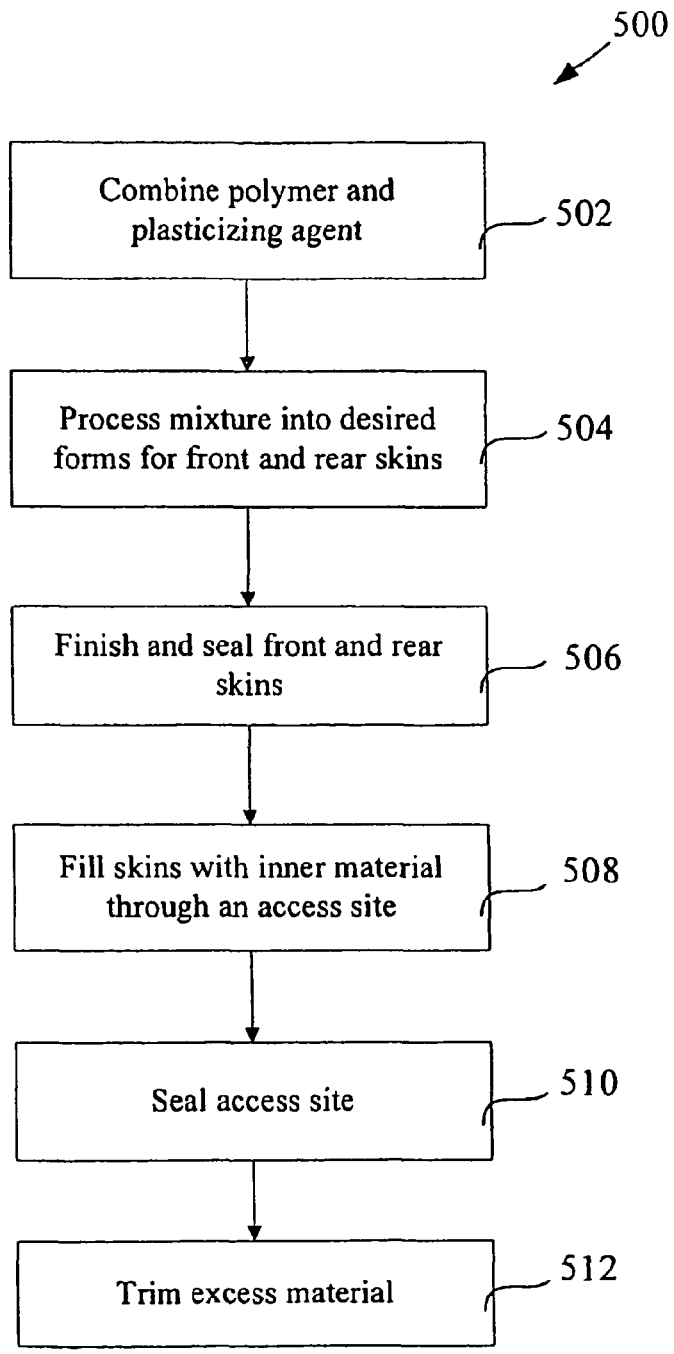
FIG. 5 is a flow diagram depicting a method of making an external breast prosthesis according to an embodiment of the present invention.

Turning to FIG. 5, a method 500 of making an external breast prosthesis according to an embodiment of the present invention can include mixing a polymer and a plasticizing agent 502 and processing the mixture into desired forms to make front and rear skins such as the various elastomeric skin forms described herein.

Suitable polymers may include, for example, triblock copolymers such as SEP, SEPS, SEBS, SEEPS, or combinations thereof. Some such polymers are sold, for example, under the trademarks SEPTON.RTM. and KRATON.RTM. In some embodiments, 100 parts by weight of one or a mixture of two or more of a hydrogenated styrene/isoprene/butadiene block copolymer are used.

Suitable plasticizing agents include, for example, a paraffinic oil, a naphtenic petroleum oil, a mineral oil, and a synthetic oligomer of polybutene, polypropylene, polyterpene, and the like.

In one example, a plasticizing oil such as CARNATION-.RTM. White Mineral Oil (Crompton Corporation, Tarrytown, N.Y.) can be combined 502 with a styrenic block copolymer such as SEPTON.RTM. TPR 4055 (Septon Company of America, Pasadena, Tex.), a hydrogenated poly(styrene-b-isoprene/butadiene-b-styrene), or polystyrene-b-poly (ethylene-ethylene/propylene)-b-polystyrene. The polymer and oil are combined, for example, at a temperature of about 130 to 165.degree. F. In some embodiments, approximately 100 pph of polymer and approximately 550 pph, or 300 to 1000 pph, of plasticizing oil may be used. The plasticizing oil may be heated prior to or after combination 502 with polymer, for example in an extruder, a molding machine or other suitable heated vessel.

In some embodiments, a stabilizer or other additive may also be included along with the polymer and/or oil. For example, pentaerythritol tetrakis(3-(3,5-di-tert-butyl-4-hydroxyphenyl)propionate) (IRGANOX.RTM. 1010, Ciba Specialty Chemicals, Inc.), provides a silky smooth texture on the skin. In one embodiment, approximately 1 to 10 pph of a stabilizer (e.g., 3.85 pph, of SEPTON.RTM.) such as IRGANOX.RTM. 1010 is added to the polymer and oil in step 502.

In step 504, the polymer/plasticizing agent mixture is processed into desired forms to create rear and front skins, such as rear skins 12, 212, 312, 412 and front skins 14, 214, 314, 414. Different methods can be used to form the mixture into the desired shapes, for example by molding or thermoforming as described in more detail with respect to FIGS. 6 and 7, respectively.

Figure 6:
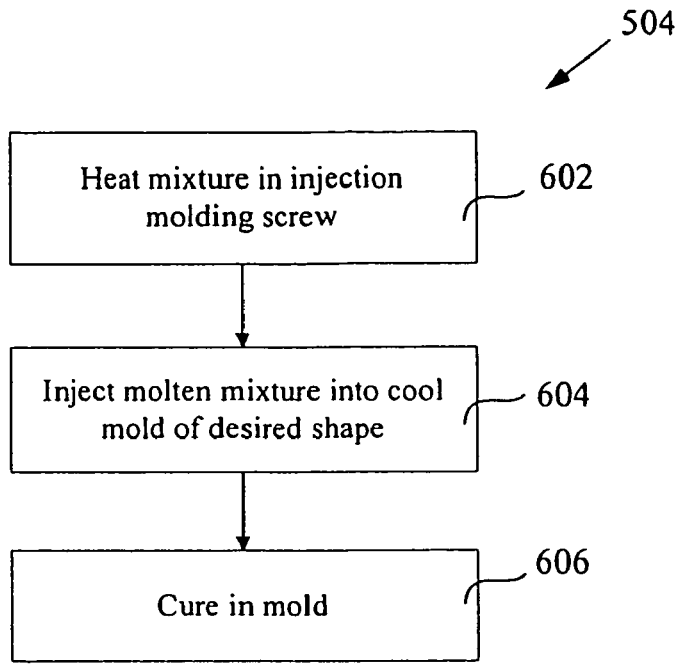
FIG. 6 is flow diagram depicting details of a processing step of FIG. 5 according to an embodiment of the present invention.

Referring to FIG. 6, an embodiment of processing 504 the skin material includes heating 602 the polymer and plasticizing agent mixture in a device such as an injection molding screw. Such heating 602 is performed at a sufficient temperature, e.g., 385-410.degree. F. or more than 410.degree. F., and for a sufficient duration, e.g., five to ten minutes or more than ten minutes, to melt the polymer and plasticizing agent into a molten mixture. Triblock copolymer elastomers melt at different temperatures depending on the molecular weight of the polymer and the amount of plasticizer used. The molding temperature therefore can range from 300 to 450.degree. F. The time required is function of the size of the melting apparatus. The process is generally faster in machines such as reciprocating screw molding machines or extruders, and it is slower in melting pots and kettles.

In step 604, the molten mixture is injected or otherwise transferred into one or more molds of a desired shape of a front or rear skin. For example, a suitable mold may be in the shape of front skin 14 and include nipple 16 as shown in FIG. 1B. Another mold may have a shape for creating rear skin 12. In other embodiments, a single mold having one or more parts may be used to create front 14 and/or rear skin 12. Color may be added to the mixture or portions of the mixture before or after injection into the mold. The mold(s) may be cooled (e.g., to 85-130.degree. F.) prior to injecting 604 the molten mixture, and such injection can be performed under vacuum or pressure to aid filling of mold cavities. After injecting 604 the mixture, it can be allowed to cool or cure 606 in the mold into the desired form, for example for a duration of approximately 60 to 100 seconds.

Figure 7:
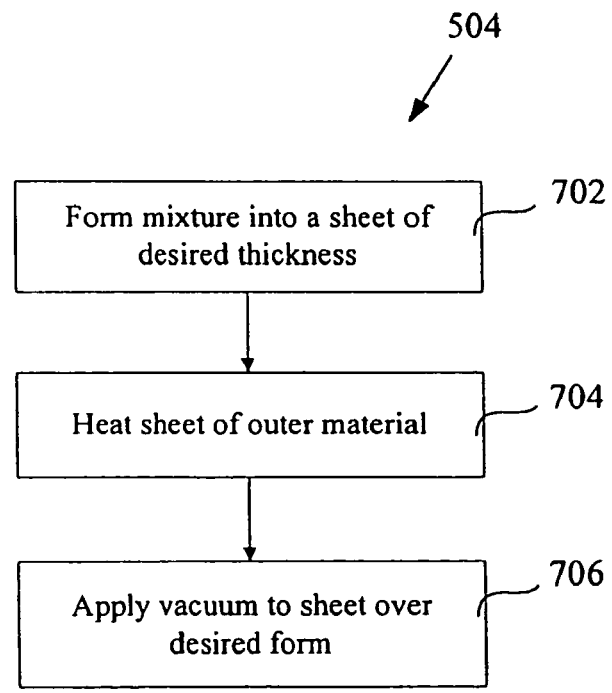
FIG. 7 is a flow diagram depicting details of a processing step of FIG. 5 according to another embodiment of the present invention.

Referring to FIG. 7, another embodiment of processing 504 the skin material for making an external breast prosthesis involves thermoforming. For example, an initial step of such process 702 can include forming the polymer/plasticizing oil mixture into one or more sheets of desired thicknesses. Such forming 702, can be accomplished, for example, by molding as described above or by pouring a molten mixture into a mold or tray or onto a surface. The mixture can be allowed to cure or cool into a sheet, e.g., an elastomeric sheet, of desired thickness. To thermoform such sheets into a desired shape, a sheet is first heated 704, for example to a temperature of approximately 90.degree. C. The heated sheet is then subjected to a vacuum over a desired form 706, such as a form of front skin 14 of FIG. 1B.

Returning to FIG. 5, after front and rear skins are formed in step 504, such skins are finished and sealed 506. In some embodiments, finishing and sealing 506 can comprise heating front and back skins to a suitable temperature, e.g., approximately 60.degree. C., and applying an adhesive to desired bonding areas on both skins. An example of a suitable adhesive is toluene, although various other adhesives are known and may be used. The bonding areas can include, for example, circumferential edge portions 22 of front 14 and rear 12 skins as shown in FIG. 1B. In multi-chambered embodiments having an inner skin or barrier such as barrier 346 of FIG. 3, such additional skin or barrier may be sealed along an edge 322 with front 314 and rear 312 skins.

After application of the adhesive, the bonding areas may be pressed together for a period of time, e.g., for several minutes, to create a seal between the front and rear skins. A powder, for example talcum powder, may be applied to one both skins to provide smooth surface characteristics. In some embodiments, the outer surface of the front skin is powdered, which the outer surface of the rear skin is not powdered and remains tacky to facilitate placement or attachment of the prosthesis to the patient or within a garment.

In other embodiments, finishing and sealing 506 can be accomplished using heat sealing. For example, 506 can include placing the front skin into a form having the desired shape of the front skin, and overlaying the back skin to align the desired bonding areas. Once the skins are aligned as desired, heat is applied to the selected bonding areas to create a seal. Such heat may be applied, for example, at 325-375.degree. F. for two to three minutes. Again, one or both skins may be powdered as described above.

In other embodiments, front and rear skins are not formed separately and later joined. Rather, the front and rear skins can be injection molded, thermoformed, or otherwise formed as a single contiguous envelope or skin surrounding a central cavity into which gel or other filling material is injected or otherwise deposited. In a specific embodiment, a hollow envelope of elastomeric skin is formed by injecting a molten elastomeric mixture as described herein into a mold and cooling the mixture. Such a mold, can have one or more parts, for example a first part configured to shape the front of the prosthesis into a form approximating a human breast, and a second part adapted to form the rear portion of the skin that joins with the front portion to create and surround a central cavity.

After the front and rear skins are finished and sealed in 506, the interior space or cavity between the sealed skins is filled 508 with inner material, e.g., by injection through an access site. As described above, inner material may be shapeless as front and rear elastomeric skins can be molded or formed into the desired breast shape that contains the inner material. Suitable inner materials include, for example, silicone gels and s. In one embodiment, a filling includes approximately 100 pph water along with, for example, 2 pph of a gelling agent. An example of a suitable gelling agent is an acrylamide such as CARBOPOL.RTM. Ultrez 21 Polymer (Noveon, Inc., Cleveland, Ohio), which is a hydrophobically modified crosslinked polyacrylate polymer. Another example of a suitable gelling agent is a carboxy methyl cellulose such as CARBOPOL.RTM. 940 (Noveon, Inc., Cleveland, Ohio). Color and/or a preservative may also be included in the hydrogel or other filling as desired.

An example of a suitable silicone gel includes, for example, RHODORSIL.RTM. Gel 4621 SLDA and Gel 4621 SLDB (Rhodia Silicone GMBH, Lubeck), each at approximately 50 parts by weight, which form into a two-component silicone elastomer that crosslinks at room temperature by polyaddition reaction. Such polymerization can be accelerated using heat up to 120.degree. C. Another example of a suitable gel includes RHODORSIL.RTM. Gel 4723SLD A and B (Rhodia Silicone GMBH, Lubeck), each at approximately 50 parts by weight.

Continuing with FIG. 5, after the skins are filled with the inner material in step 508, the hole or access site through which the inner material was added is sealed in step 510. Such sealing may be accomplished, for example, using adhesive or a heat seal as described above, by using a patch, or by any other method that effectively seals the skin(s) to prevent leakage of the inner material. In step 512, excess skin material and/or inner material can be trimmed away from the seal or bonding lines. The finished prosthesis may also be cleaned, for example, using a water and alcohol solution, checked using a suitable quality control procedure, and packaged.

Figure 8:
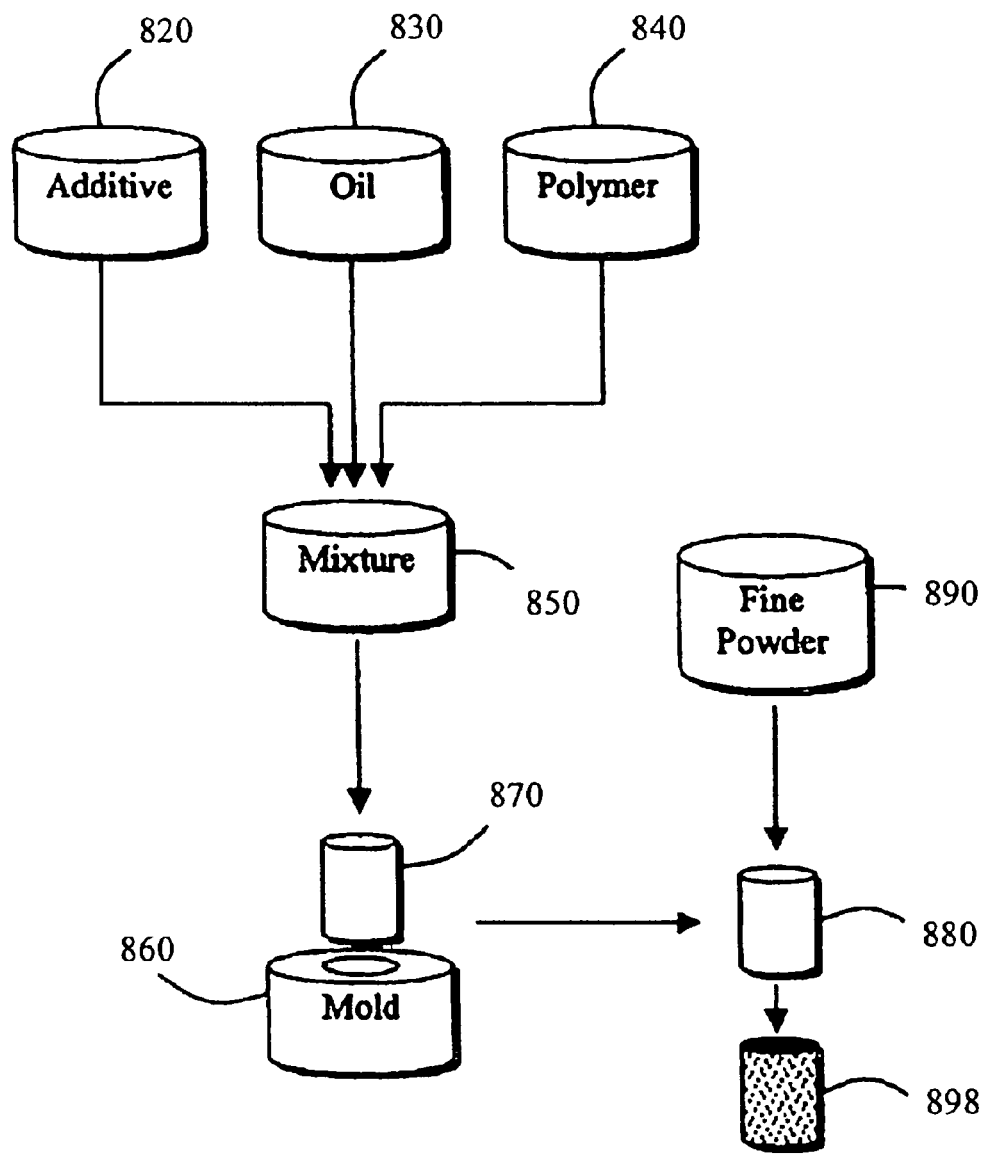
FIG. 8 is a schematic diagram depicting another embodiment of a method of making an elastomer for use in an external breast prosthesis.

Referring to FIG. 8, a method of making an elastomer for use in an external breast prosthesis according to an embodiment of the present invention can include use of one or more additives to provide desired surface characteristics of the front and/or rear skins. Briefly, a process of making such an elastomer can include mixing an additive 820, a plasticizing oil 830 and a polymer 840 to form a mixture 850. For example, additives, e.g., such as one or more of those additives listed in Table I below, may be used to create a powder-like precipitate that diffuses to the surface of the elastomer during and/or after forming or cooling of the elastomer, thus reducing tackiness of the elastomer where such surface characteristics are desired.

Plasticizing oil 830 may be heated prior to the addition of polymer 840 and/or additive 820. Mixture 850 can be melted, for example in an extruder, a molding machine or other suitable heated vessel so that the additives become soluble in molten mixture 850 and remain in stable solution in the molten mixture 850.

Figure 9:
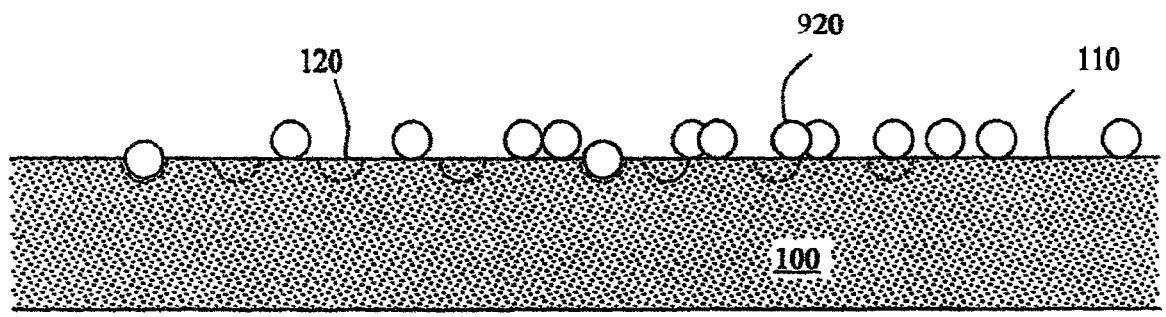
FIG. 9 is a side-elevated, partially sectional diagrammatic view of the elastomer surface showing the cratered surface according to an embodiment of the invention.

Molten mixture 850 can then be molded 860 or otherwise shaped into any desired shape or form, for example into a front or rear prosthetic breast skin as described above. As illustrated in FIG. 9, when allowed to cool, the mixture can solidify and form elastomer 880. The additives 920 can begin to diffuse to the surface of elastomer 880 upon completion of the solidification process. Precipitation may be initiated by seeding the surface of elastomer 680 with fine powder 890 such as talcum powder, for example during the cooling process. Elastomer 880 can then be cooled to solidify elastomer 898, whereby additive 820 may precipitate to the surface of solidified elastomer 898, e.g., in the form of a dry powder.

If the plasticizing oil is heated, an appropriate temperature range may be about 130 to 165.degree. F. As described above with respect to FIG. 5, plasticizing oils such as paraffinic oils, naphtenic petroleum oils, mineral oils, and synthetic liquid oligomers of polybutene, polypropylene, polyterpene, and the like may be used. Optionally, a seeding of the oil may also be effected, with an insoluble fine powder such as talcum powder. Preferably, 300 to 1000 parts by weight of the plasticizing oil may be used.

An additive can then be mixed in the plasticizing oil, optionally with seed, for a defined time, e.g., approximately 10 minutes, at a temperature of preferably 130 to 165.degree. F. The additive may also be added to the plasticizing oil with or after the addition of the polymer. Table I discloses as examples some additives that may be suitable in this process. TABLE-US-00001 TABLE I Chemical Name 1 Tetrakis (2,4-di-tert-butylphenyl) [1,1-biphenyl]-4,4'-diylbisphosphonite 2 Tris (2,4-ditert-butylphenyl) phosphate 3 Butanedioic acid, dimethylester, polymer with 4-hydroxy-2,2,6,6-tetramethyl-1-piperidine ethanol 4 2,6-di-tert-butyl-4-(4,6-bis(octylthio)-1,3,5-triazin-2-ylamino) phenol 5 3,3',3',5,5',5'-hexa-tert-butyl-a,a',a'-(mesitylene-2,4,6-triyl) tri-p-cresol 6 Pentaerythritol Tetrakis (3-(3,5-di-tert-butyl-4-hydroxphenyl)propionate) 7 Phenol,2-(5-chloro-2H-benzotriazole-2-yl)-6-(1,1-dimethylethyl)-4-methyl 8 Thiodiethylene bis[3-(3,5-di-tert-butyl-4-hydroxyphenyl)propionate] 9 Calcium phosphonate 10 Dioctadecyl 3,3'-thiodipropionate 11 Didodecyl 3,3'-thiodipropionate 12 2-(1,1-dimethylethyl)-6-[[3-(1,1-dimethylethyl)-2-hydroxy-5-methylphenyl]methyl-4-methylphenyl acrylate 13 N,N'-hexane-1,6-diylbis (3-(3,5-di-tert-butyl-4-hydroxyphenylpropionamide))

The tris(2,4-ditert-butylphenyl) phosphate listed in Table I is a white crystalline powder, commonly used as a phosphate processing stabilizer for polycarbonate and polyolefins. It can be used, for example, in combination with phenolic antioxidants and can aid in color stability and polymer viscosity. The butanedioic acid listed in Table I is also known as succinic acid. It is a colorless crystalline solid with a melting point of 185-187.degree. C., soluble in water, slightly dissolved in ethanol, ether, acetone and glycerine, but not dissolved in benzene, carbon sulfide, carbon tetrachloride and oil ether. A common method of synthesis of succinic acid is the catalytic hydrogenation of maleic acid or its anhydride.

In some embodiments, 0.5 to 10 parts of one or more additives can be mixed with the plasticizing oil or with the plasticizing oil and polymer mixture. The additives can be solid at room temperature (25.degree. C.) and soluble in the molten mixture. The additives can have higher solubility in the triblock copolymer elastomers at higher temperatures than at room temperatures. The addition of such additives can be in a predetermined proportion that exceeds the solubility of the additives in the elastomer at room temperature. The addition of such additives to the mixture of polymers and plasticizing oil can be made either prior to the melting of the mixture in a heated vessel or when the mixture is in its molten state.

In a specific embodiment, a polymer or mixture of polymers is added to the plasticizing oil or to the mixture of plasticizing oil and additives for 30 minutes at 130.degree. F. to 165.degree. F. starting temperature. As described above, suitable polymers may be any triblock copolymer, including for example styrenic triblock copolymers such as SEP, SEPS, SEBS or SEEPS. Preferably, 100 parts by weight of one or a mixture of two or more of a hydrogenated styrene/isoprene/butadiene block copolymer are used.

The mixture containing the plasticizing oil, the additive and the polymer can be melted in an extruder, a reciprocating screw molding machine, or a heated vessel at about 415.degree. F., for example. As mentioned earlier, the additive may be added to the mixture of polymers and plasticizing oils either prior to the melting of the mixture or in the melt phase.

The mixture is maintained at or above melting temperature, with or without mixing, for an amount of time necessary to ensure adequate dissolution and dispersion of the additives in the mixture. The time required to effect an adequate mixture can be a function of the triblock copolymer used and the equipment used to melt the mixture. For high molecular weight copolymers, such as SEPTON.RTM. 4055, for example, the time at or above melting temperature can be considerably higher than for a lower molecular weight copolymer such as SEPTON.RTM. 4033. Also reciprocating screw type injection molding machines or plastic extruders require less time at or above melting temperature than melting pots or vats. Also, when using melting pots and vats the time at or above melting temperature can be dependent on the size of the pot. Thus, in some embodiments utilizing high molecular weight polymers, a typical time for processing the mixture is, for example, 10 to 30 minutes in a reciprocating screw type injection molding machine or an extruder, and 4 to 16 hours in a melting pot or vat. In embodiments utilizing low molecular weight polymers, a typical time for processing the mixture is, for example, 5 to 15 minutes in a reciprocating screw, and 2 to 8 hours in a melting pot or vat.

After the expiration of such amount of time, the mixture can be molded, extruded, cast or otherwise formed, and then allowed to cool or can be actively cooled. In either event, the mixture may undergo a phase change from liquid to semi-solid or solid. The additives can remain dissolved in the molten mixture, where upon solidification of the mixture, the mixture becomes an elastomer and precipitation of the additives from the elastomer begins.

More particularly, where the mixture is first melted and then cooled, at a controlled temperature profile, precipitation of the additives can occur within the elastomer as the solubility parameters of the additive in the elastomer are exceeded. The solubility of the additives can decrease as the temperature of the elastomer falls. Precipitation may be initiated by seeding the surface of the elastomer with a fine powder such as talcum powder. Precipitation may also be initiated by mechanical solicitation of the elastomer, such as stretching or other deformation of the elastomer.

The size of the particles of the precipitated phase can be a function of the time temperature profile maintained during the cooling period and of the mechanical stress to which the elastomer is subjected. More particularly, the particles may increase in size as the cooling rate is decreased and as the amount of mechanical deformation is decreased. A faster cooling rate and greater mechanical deformation can produce smaller particle sizes.

The diffusion rate of precipitate to the surface of the liner can also increase as the stress to strain ratio decreases, i.e., the diffusion rate increases as the modulus of the elastomer, or elastic limit stress, decreases.

Molding, casting or extruding of the molten mixture can be conducted at a mold temperature of, for example, 95-130.degree. F. for 5-10 minutes. The molded elastomer can be removed from the mold after the expiration of such period of time. Although stretching is not required, stretching of the elastomer by about 50% may improve the diffusion rate. Other mechanical deformation of the elastomer may be substituted for or added to the stretching.

A step of aging at a controlled temperature profile may also be performed. For example, such aging may be accomplished at a temperature of 20-32.degree. F. for one (1) hour.

The precipitated phase can diffuse to the surface of the elastomer and collect as a powder on its surface. After removal of the surface powder, by wiping, washing, or the like, additional powder can migrate to the surface of the elastomer. The process can be repeated until the saturation level at room temperature of the precipitate phase in the elastomer is reached. The process of diffusion to the surface may then stop.

Details regarding suitable elastomers and additives, and methods of making articles incorporating such elastomers, may also be found in the applicant's co-pending U.S. patent application Ser. No. 10/817,612, filed Apr. 2, 2004, entitled Precipitation of Additives in Over-Saturated Triblock Copolymer Elastomers, which is incorporated by reference herein in its entirety.

EXAMPLES

In a particular example, an external breast prosthesis according to an embodiment of the present invention was made that has front and rear skins comprising a mixture of styrenic block copolymer (SEPTON.RTM. 4055, a SEEPS) at 100 pph, an additive (IRGANOX.RTM. 1010, a pentaerythritol tetrakis(3-(3,5-di-tert-butyl-4-hydroxyphenyl) propionate)) at 2.9 to 3.85 pph, and plasticizing oil (CARNATION.RTM. 70) at 500 to 700 pph. The mixture was heated in an injection molding screw to 385-410.degree. F., injected into a cool mold (85-110.degree. F.), and cured for 60 to 100 seconds. In this example, front and rear skins were molded separately, and then bonded together to form a perimeter seal using an adhesive as described above with respect to FIG. 5. One skilled in the art will appreciate that other methods of joining or sealing the skins may be used, or the front and rear skins could have been formed in the same mold as a contiguous skin.

In this example, front skin was molded in the shape of a human breast and included an molded elastomeric nipple. Rear skin included a fabric bonded with its exterior surface. After the front and rear skins were sealed, a gel material was injected into the cavity between the front and rear skins. In this particular example, the gel was a hydrogel comprised of approximately 375 g of water, 20 g of wet expanded microspheres, and 3 g of LUQUASORB.RTM. 101 (BASF), a super-absorbent polymer. In other examples, a neutralized polyacrylate solution replaced the BASF solution. In still other examples, various other s (e.g., a neutralized polyacrylate, acrylamide, carboxylmethyl cellulose, or other absorbent or super-absorbent polymers) and silicone gels were used.

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A method of making an external breast prosthesis, comprising: (a) mixing together a polymer and a plasticizing oil and at least one non-volatile additive to form a mixture; (b) heating the mixture; (c) forming the mixture into a front elastomeric skin, wherein the front elastomeric skin has a shape approximating a form of a human breast; (d) cooling the mixture thereby allowing the non-volatile additive to precipitate to the outer surface of the outer skin whereby a cratered outer surface is formed; (e) forming a rear elastomeric skin having a shape adapted to seal with the front elastomeric skin; (f) sealing the front elastomeric skin with the rear elastomeric skin so as to form a cavity therebetween; and (g) filling a cavity between the front elastomeric skin and the rear elastomeric skin with a gel.

2. The method of claim 1, wherein the polymer comprises a triblock copolymer comprising styrene and at least one of ethylene, butadiene, butylene, isoprene, or propylene.

3. The method of claim 2, wherein the triblock copolymer is any of polystyrene-b-poly(ethylene/propylene), polystyrene-b-poly(ethylene/propylene)-b-polystyrene, polystyrene-b-poly(ethylene/butylene)-b-polystyrene, or polystyrene-b-poly(ethylene-ethylene/propylene)-b-polystyrene.

4. The method of claim 1, wherein the plasticizing oil is any of a paraffinic oil, naphtenic oil, a mineral oil, or a synthetic oligomer comprising polybutene, polypropene, or polyterpene.

5. The method of claim 1, wherein the gel comprises any of a silicone gel, a hydrogel, or a combination thereof.

6. The method of claim 1, further comprising forming an intermediate barrier, and wherein: the step (e) of sealing the front elastomeric skin with the rear elastomeric skin further comprises sealing the intermediate barrier between the front skin and said the skin such that the cavity comprises a front cavity between the front skin and the intermediate barrier and a rear cavity between the rear skin and the intermediate barrier; and the step (f) of filling the cavity further comprises filling the front cavity with the gel and filling the rear cavity with a second material.

7. The method of claim 6, wherein the gel comprises any of a silicone gel, a hydrogel, or a combination thereof.

8. The method of claim 7, wherein the second material comprises any of a gel, a foam, a liquid, a polymer, or any combination thereof.

9. A method of making an external breast prosthesis, comprising: (a) mixing together a polymer and a plasticizing oil and at least one non-volatile additive to form a mixture; (b) heating the mixture; (c) forming the mixture into an elastomeric skin surrounding a hollow cavity, said skin having a front portion configured and dimensioned to approximate the shape of a human breast; (d) cooling the mixture thereby allowing the non-volatile additive to precipitate to the outer surface of the elastomeric skin whereby a cratered outer surface is formed; and (e) filling the cavity with a gel.

10. The method of claim 9, wherein the step (c) of forming the mixture into the elastomeric skin comprises: transferring the heated mixture into a mold; and cooling the mixture to form the elastomeric skin.

11. The method of claim 9, wherein the polymer comprises any of polystyrene-b-poly(ethylene/propylene), polystyrene-b-poly(ethylene/propylene)-b-polystyrene, polystyrene-b-poly(ethylene/butylene)-b-polystyrene, or polystyrene-b-poly(ethylene-ethylene/propylene)-b-polystyrene.

12. The method of claim 9, wherein the gel comprises a silicone gel, a hydrogel, or a combination of a silicone gel and a hydrogel.

* * * * *